United States Patent [19]

Müller

[11] Patent Number: 4,764,604

[45] Date of Patent: Aug. 16, 1988

[54] DERIVATIVES OF GAMMA-CYCLODEXTRIN

[75] Inventor: Bernd W. W. Müller, Flintbek, Fed. Rep. of Germany

[73] Assignee: Janssen Pharmaceutica N.V., Beerse, Belgium

[21] Appl. No.: 833,622

[22] Filed: Feb. 27, 1986

[30] Foreign Application Priority Data

Mar. 15, 1985 [GB] United Kingdom ............... 8506792

[51] Int. Cl.$^4$ ............................................. C08B 37/16
[52] U.S. Cl. .................................................... 536/103
[58] Field of Search ......................................... 536/103

[56] References Cited

U.S. PATENT DOCUMENTS

| | | | |
|---|---|---|---|
| 3,459,731 | 8/1969 | Gramera et al. | 536/103 |
| 4,535,152 | 8/1985 | Szejtli et al. | 536/103 |
| 4,596,795 | 6/1986 | Pitha | 536/103 |
| 4,727,064 | 2/1988 | Pitha | 514/965 |

*Primary Examiner*—Ronald W. Griffin
*Attorney, Agent, or Firm*—Geoffrey G. Dellenbaugh

[57] ABSTRACT

This invention relates to γ-cyclodextrin ethers and mixed ethers wherein the ether substituents are $C_1$–$C_6$ alkyl, hydroxy $C_1$–$C_6$ alkyl, carboxy $C_1$–$C_6$ alkyl or ($C_1$–$C_6$ alkyloxycarbonyl) $C_1$–$C_6$ alkyl; provided that hydroxypropyl is not a sole substituent.

17 Claims, No Drawings

DERIVATIVES OF GAMMA-CYCLODEXTRIN

BACKGROUND OF THE INVENTION

The present invention is concerned with new ethers of γ-cyclodextrin, their preparation and their use as complexants for chemicals and pharmaceuticals.

γ-cyclodextrin (γ-CD) is a cyclic oligosaccharide consisting of 8 glucose units which are joined together by α(1-4) linkages.

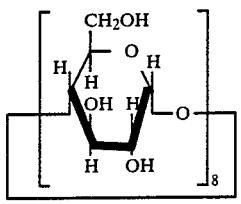

γ-CD is prepared by the enzymatic cleavage and religation of starch and a subsequent separation from the thus obtained cyclodextrin mixture containing i.a. α-cyclodextrin (containing 6 glucose units), β-cyclodextrin (β-CD) (7 glucose units) and γ-cyclodextrin (γ-CD).

Cyclodextrins are known in the art to possess the ability to form inclusion complexes and to have concomitant solubilizing properties. An exhaustive review which describes such complexes and their properties can be found in W. Sänger, Angewandte Chemie, 92, 343–361 (1981).

Derivatives of cyclodextrins are also known to possess the above-mentioned properties. Said derivatives have been reviewed in an article by A. P. Croft and R. A. Bartsch in Tetrahedron, 39, 1417–1474 (1983). More particularly, the German Offenlegungsschrift No. DE 3118218 discloses the 2,6-dimethyl derivatives of β-CD, while in U.S. Pat. No. 3,459,731 there are described hydroxyethyl, hydroxypropyl and hydroxypropyl/hydroxyethyl ethers of β-CD. Furthermore, in U.S. patent application Ser. No. 6-603,839 there is described the use of specific derivatives of cyclodextrines to improve the systemic administration of sex hormones. Most of the cyclodextrin derivatives presently known in the art are derived from β-CD, while the derivatives of α-CD and particularly of γ-CD remain relatively unknown.

The use of derivatives of β-CD has the following advantages. β-CD is only poorly water soluble and therefore it is disadvantageous to use it as a complexant and solubilizer. Derivatives of β-CD on the other hand, due to their increased solubility, are more suitable complexants and solubilizers. In contrast herewith, α-CD and γ-CD having an excellent water solubility do not need such substitutions. Hence, it is obvious to use unsubstituted γ-CD (and α-CD) as complexant and solubilizer. Particularly for γ-CD, a number of such complexes with various useful compounds can be found in e.g. Int. J. Pharm. 10, 1–15 (1982) with steroid hormones, in Acta Pharm. Suec. 20, 11–20 (1983) with flurtripofen, in Chem. Pharm. Bull. 32, 286–291 (1983) with spirolacton and in Acta Pharm. Suec. 20, 287–294 (1983) with proscillaridin.

γ-CD does not form such inclusion complexes with any given compound. Often, such complexation is only established in the lower concentration range. At higher concentrations of γ-CD, the formed complex is precipitated.

It has now been found that an appropriately alkylated, hydroxy-alkylated, carboxyalkylated or (alkyloxycarbonyl)alkylated form of γ-CD or a mixed ether thereof prevents the crystallization of such complexes. The advantages of γ-CD over its lower homologues, i.e. its larger cavity resulting in a superior propensity to form inclusion complexes, its favourable toxicological properties and the fact that it can be cleaved enzymatically by α-amylase (in contrast with β-CD), can therefore fully be exploited.

γ-CD contains three free hydroxy functions per glucose unit which can completely or partially be derivatized. In view of this, the average degree of substitution (D.S.) is introduced, which is the average number of substituted hydroxy functions per glucose unit. Said D.S. can vary from its minimal value 0.125 up to its maximal value 3. In the latter case all 24 hydroxy groups are substituted, while in the former case only one is substituted. A minimal D.S. is especially preferred when γ-CD is used as solubilizer of pharmaceuticals for use in parenteral applications, while a higher D.S. is preferred when used in technical applications, such as, for example, for pesticides or enzymes. In the latter instance, the higher D.S. causes that also those hydroxy groups are functionalized which are located in the cavity of the γ-CD molecule. Consequently, the diameter of the cavity is decreased. By selecting the appropriate D.S. the size of the cavity can be adapted in order to obtain the optimum space required for a certain molecule to appropriately fit into the cavity of the cyclodextrin.

When introducing hydroxyalkyl substitutions on γ-CD, the hydroxy function of the thus obtained hydroxyalkyl ether group can further be hydroxyalkylated, generating multiple substitutions on one particular OH-group. In such cases the term average molar substitution (M.S.) is introduced. Said M.S. is defined as the average number of moles of the substituting agent per glucose unity. In view of this, it is evident that the M.S. can be greater than 3 and has, theoretically, no upper limit.

DESCRIPTION OF THE PREFERRED EMBODIMENTS

The present invention is concerned with novel γ-CD derivatives, said novel γ-CD derivatives being γ-CD substituted with $C_1$–$C_6$ alkyl, hydroxy $C_1$–$C_6$ alkyl, carboxy $C_1$–$C_6$ alkyl or $C_1$–$C_6$ alkyloxycarbonyl $C_1$–$C_6$ alkyl or mixed ethers thereof.

In the foregoing definitions the term "$C_1$–$C_6$-alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Preferred compounds are those γ-CD derivatives being γ-CD substituted with $C_1$–$C_3$ alkyl, hydroxy $C_2$–$C_4$ alkyl, carboxy $C_1$–$C_2$ alkyl or ($C_1$–$C_2$ alkyloxycarbonyl) $C_1$–$C_2$ alkyl or mixed ethers thereof.

Particularly preferred new compounds are the methyl, ethyl, isopropyl, hydroxyethyl, hydroxypropyl, hydroxybutyl, carboxymethyl and carboxyethyl substituted γ-cyclodextrins and further the (methyl)(hydroxyethyl), (methyl)(hydroxypropyl) and (methyl)(hydroxyethyl)(carboxymethyl) substituted γ-cyclodextrins having a D.S. or M.S. of from 0.125 to 3, more preferably of from 0.3 to 2.

The compounds of the present invention can generally be prepared by reacting the starting γ-CD with an appropriate O-alkylating agent or a mixture of such agents in a concentration being selected so that the desired D.S. is obtained. The said reaction is preferably conducted in a suitable solvent in the presence of an appropriate base. An appropriate O-alkylating agent is, for example, an alkyl, hydroxyalkyl, carboxyalkyl or (alkyloxycarbonyl)alkyl halide or sulfonate, e.g. methyl chloride, ethyl bromide, propyl methylsulfonate, ethyl chloroacetate, α-chloroacetic acid; or an oxirane, e.g. oxirane, methyloxirane. Suitable solvents are, for example, water; an alcohol or polyalcohol, e.g. methanol, ethanol, 1-propanol, 2-propanol, 1-butanol, 1,2-ethanediol, 1,2-propanediol and the like; a ketone, e.g. 2-propanone, 2-butanone, 4-methyl-2-pentanone, and the like; an ether or polyether, e.g. ethoxyethane, 2-(2-propyloxy)propane, tetrahydrofuran, 1,2-dimethoxyethane and the like; and $C_1$–$C_4$-alkyloxy-$C_2$–$C_3$-alkanol and mixtures of such solvents. An appropriate base is, for example, an alkali or earth alkaline metal hydroxide, e.g. sodium hydroxide, potassium hydroxide; or an alkali or earth alkaline metal hydride or amide, e.g. sodium hydride, calcium hydride, sodium amide and the like bases.

Preferably the said O-alkylation reaction is conducted with 0.1 to 3 parts by weight of water per part by weight γ-CD in case there is no organic solvent used, and with 1 to 40 parts by weight organic solvent per part by weight γ-CD in case no water is used.

In a particularly preferred way of preparing the compounds of the present invention, the reaction mixture containing the starting γ-CD, the solvent, base and O-alkylating agent is heated in an autoclave at a temperature comprised between 30° and 200° C. Depending on the reactivity of the O-alkylating agent, the reaction mixture is allowed to react at this temperature for 15 minutes up to 24 hours. Subsequently, the mixture is acidified and the reaction product is isolated and purified by standard separation and purification procedures such as, for example, column chromatography, ultra filtration, centrifugation, and dried.

The compounds of the present invention can also be converted into each other. For example, the (alkyloxycarbonyl)alkyl substituted γ-cyclodextrines may conveniently converted to the corresponding carboxyalkyl substituted γ-cyclodextrines following art-known saponification procedures, e.g. by treating the starting compounds with an aqueous acidic or basic solution.

The compounds of the present invention are useful due to their ability to form inclusion complexes having a stabilizing effect on the complexed compounds, and due to their concomitant solubilizing activity. Compounds exhibiting a significantly increased water solubility and improved stability after having been transferred to inclusion complexes with the above-mentioned γ-CD derivatives, are those having the required shape and size, i.e. which fit into the cavity. The size of the cavity can be adapted by selecting the appropriate γ-CD derivatives having a suitable D.S. Examples of such compounds are, for example, non-steroid antirheumatic agents, steroids, cardiac glycosides and derivatives of benzodiazepine, benzimidazole, piperidine, piperazine, imidazole, triazole, pyridazine, 1,2,4-triazinedione or 2,3,5,6-tetrahydro-imidazo[2,1-b]thiazoles, or amides, hydratropic acid derivatives or trialkylamines, whereby the derivatives of benzodiazepine, benzimidazole, piperidine, piperazine, imidazole, triazole, pyridazine, 1,2,4-triazinedione or 2,3,5,6-tetrahydro-imidazo[2,1-b]thiazole, or amides, hydratropic acid derivatives or trialkylamines are preferred.

Useful benzimidazole derivatives are thiabendazole, fuberidazole, ciclobendazole, oxibendazole, parbendazole, cambendazole, mebendazole, fenbendazole, flubendazole, albendazole, oxfendazole, nocodazole and astemizole.

Suitable piperidine derivatives are diphenoxylate, phenoperidine, haloperidol, haloperidol decanoate, bromperidol decanoate, bromperidol, moperone, trifluperidol, pipamperone, piritramide, fentanyl, benperidol, droperidol, benzitramide, benzetimide, domperidone, sufentanil, carfentanil, alfentanil, dexetimide, milenperone, difenoxin, fluspirilene, penfluridol, pimozide, lorcainide, loperamide, astemizole, ketanserine, levocabastine, cisapride, altanserin, ritanserin, 3-[2-[4-(4-fluorobenzoyl)-1-piperidinyl]ethyl]-2,7-dimethyl-4H-pyrido[1,2-a]pyrimidin-4-one, 3-[2-[4-[bis(4-fluorophenyl)methylene]-1-piperidinyl]ethyl]-2-methyl-4H-pyrido[1,2-a]pyrimidin-4-one and 3-[2-[4-[[3-(2-furanylmethyl)-3H-imidazo[4,5-b]pyridin-2-yl]amino]-1-piperidinyl]ethyl]-2-methyl-4H-pyrido[1,2-a]pyrimidin-4-one. Suitable piperazine derivatives include azaperone, fluanisone, lidoflazine, flunarizine, mianserine, oxatomide, mioflazine, clocinizine and cinnarizine.

Examples of suitable imidazole derivatives are metronidazole, ornidazole, ipronidazole, tinidazole, isoconazole, nimorazole, miconazole, burimamide, metiamide, metomidate, enilconazole or imazalil, etomidate, econazole, clotrimazole, carnidazole, cimetidine, doconazole, sulconazole, parconazole, orconazole, butoconazole, triadiminole, tioconazole, valconazole, fluotrimazole, ketoconazole, oxiconazole, lombazole, bifonazole, oxmetidine, fenticonazole, tubulazole and (Z)-1-[2-chloro-2-(2,4-dichlorophenyl)ethenyl]-1H-imidazole.

As suitable triazole derivatives there may be mentioned virazole, azaconazole, etaconazole, propiconazole, penconazole, itraconazole and terconazole.

Useful pyridazine derivative are, for example, 3-chloro-6-[3,6-dihydro-4-(3-methylphenyl)-1(2H)-pyridinyl]pyridazine, 3-methoxy-6-[4-(3-methylphenyl)-1-piperazinyl]pyridazine and the compounds of Publ. Eur. Pat. Appl. No. 0,156,433.

Useful 1,2,4-triazinediones are, for example, 2-chloro-α-(4-chlorophenyl)4-(4,5-dihydro-3,5-dioxo-1,2,4-triazin-2(3H)-yl)benzeneacetonitrile, 2,6-dichloro-α-(4-chlorophenyl)-4-(4,5-dihydro-3,5-dioxo-1,2,4-triazin-2(3H)-yl)benzeneacetonitrile and the compounds of Publ. Eur. Pat. Appl. No. 0,170,316.

Useful trialkylamines are, for example, diisopromine, prozapine.

Useful 2,3,5,6-tetrahydro-imidazo[2,1-b]thiazoles comprise, for example, tetramisole or levamisole.

Useful amides are, for example, closantel, ambucetamide, isopropamide, buzepide metiodide, dextromoramide.

A useful hydratropic acid derivative is, for example, suprofen.

Particularly valuable pharmaceutical compositions are obtained when converting etomidate, ketoconazole, tubulazole, itraconazole, levocabastine or flunarizine into a water-soluble form using the complex forming agents of the invention. Such compositions are therefore a special subject of the present invention.

The invention is further directed to a method of preparing compositions of sparingly water-soluble or water-instable compounds which method is characterized by dissolving the γ-cyclodextrin ether in water and adding thereto the selected compound as well as optionally drying the solution of the formed inclusion compound using methods known per se. Formation of the solution may preferably take place at temperatures between 15° and 35° C.

The drug is suitably added batchwise. The water may further comprise physiologically compatible compounds such as sodium chloride, potassium nitrate, glucose, mannitol, sorbitol, xylitol or buffers such as phosphate, acetate or citrate buffer.

Using γ-cyclodextrin ethers in accordance with the invention it is possible to prepare commonly known application forms of drugs for oral, parenteral, topical, rectal or vaginal application, e.g. infusion and injection solutions, drop solutions (e.g. eye drops or nasal drops), sprays, tablets, powders, capsules, aerosols, sirups, jellies, ointments, medical baths, rectalia and vaginalia.

The aqueous solutions may further comprise suitable physiologically compatible preserving agents such as, for example, quaternary ammonium soaps, chlorbutanol, phenoxetol, bromopol, and the like, and also anti-oxidantia, such as, for example, ascorbic acid.

For the preparation of solid formulations the solutions of the inclusion compounds are dried using conventional methods; thus the water may be evaporated in a rotation evaporator or by lyophilisation. The residue is pulverized and, optionally after addition of further inert ingredients, converted into uncoated or coated tablets, suppositories, capsules, creams or ointments.

EXAMPLES

The following examples are meant to illustrate and not to limit the present invention in all its aspects. Unless stated otherwise, all parts therein are by weight.

A. PREPARATION EXAMPLES

Example 1

1 Part of γ-CD and a solution of 1.5 parts of sodium hydroxide in 1.5 parts of water were mixed in an autoclave. Then there were added 3 parts of methyl chloride and 0.5 parts of methyloxirane. The mixture was heated for 1 hour at 65° C. and subsequently for 2 hours at 100° C. After cooling, the remaining methyloxirane was expelled and the reaction mixture was neutralized with hydrochloric acid. The volatile components were evaporated and the remainder was filtered. The filtrate was liberated from sodium chloride over an ion exchanger and subsequently freeze-dried, yielding the (methyl)-(hydroxypropyl) derivative of γ-CD. Following the same procedures and using the appropriate starting materials the (ethyl)(hydroxyethyl) derivative of γ-CD was also prepared.

Example 2

In an autoclave there were mixed 2.5 parts of 1,2-dimethoxyethane, 1 part of γ-CD and a solution of 1 part of sodium hydroxide in 1.2 parts of water. To this mixture, there were added 2 parts of oxirane and the whole was heated to 110° C. for 5 hours. After cooling, the remaining oxirane was expelled and the reaction mixture was neutralized with hydrochloric acid. The volatile components were evaporated and the remainder was filtered. The filtrate was subsequently liberated from sodium chloride over an ion exchanger and subsequently freeze-dried, yielding the hydroxyethyl derivative of γ-CD with a M.S. of 0.77.

Following the same procedures and using appropriate starting materials there was also prepared the 2-hydroxypropyl derivative of γ-CD with a M.S. of 0.66.

Example 3

1 Part of γ-CD, 3 parts of 1,2-dimethoxyethane and 1.5 parts of sodium hydroxide in 1.5 parts of water were mixed in an autoclave. Subsequently, there were added 4 parts of chloromethane and the whole was heated at 120° C. for 4 hours. After cooling the reaction mixture was neutralized with hydrochloric acid and the volatile components evaporated. The remainder was filtered and the filtrate was liberated fom sodium chloride over an ion exhanger and subsequently freeze-dried, yielding the methyl derivative of γ-CD with a D.S. of 1.49.

Following the same procedures and using the appropriate starting materials there were also prepared the methyl derivative of γ-CD with a D.S. of 0.13; the carboxymethyl derivative of γ-CD with a D.S. of 0.86; and the (ethoxycarbonyl)methyl derivative of γ-CD; the ethyl derivative of γ-CD; the butyl derivative of γ-CD; the isobutyl derivative of γ-CD; the isopropyl derivative of γ-CD; the carboxyethyl derivative of γ-CD; the 3-hydroxypropyl derivative of γ-CD; and the 4-hydroxybutyl derivative of γ-CD.

B. EXAMPLES ILLUSTRATING THE PROPERTIES OF THE γ-CD DERIVATIVES

Example 4

Starting from a 5% stock solution of a particular γ-CD derivative in a phosphate buffer of pH 7.4, a dilution series was obtained with concentrations varying of from 0% to 5% with 0.5% steps. 3 ml of these solutions were pipetted into a closed container containing an appropriate amount of progesteron. After 5 days shaking at 25° C., the thus obtained mixture was filtered over a membrane filter (pore diameter: 0.22 μm), and the content of progesteron was determined with high pressure liquid chromatography (using a column of 25 cm length; 5 mm internal diameter; packed with 5 μm ODS-hypersil (RP-18); eluent: acetonitrile/water; U.V. detection). The results of these concentration measurements for a number of the γ-CD derivatives of the present invention and for unsubstituted γ-CD gathered in the following table.

TABLE

Content of progesteron in solutions containing various concentrations of γ-CD derivative and γ-CD.

| concentration of γ-CD derivative in % (weight by volume) | content of progesteron in μg/ml | | | | | |
|---|---|---|---|---|---|---|
| | unsubstituted γ-CD | methyl substituted D.S. = 0.13 | methyl substituted D.S. = 1.49 | carboxymethyl subst. M.S. = 0.86 | hydroxy ethyl subst. M.S. = 0.77 | hydroxy propyl subst. M.S. = 0.66 |
| 0 | 5.9 | 5.9 | 5.9 | 5.9 | 5.9 | 5.9 |
| 0.5 | 425 | 488 | 379 | 102 | 234 | 302 |
| 1 | 343 | 972 | 748 | 209 | 452 | 582 |
| 1.5 | 275 | 1458 | 1144 | 313 | 673 | 872 |
| 2 | 203 | 1902 | 1470 | 417 | 860 | 1165 |
| 2.5 | 163 | 2149 | 1888 | 517 | 1055 | 1431 |
| 3 | 93 | 2258 | 2260 | 610 | 1291 | 1704 |
| 3.5 | 60 | 2392 | 2686 | 79 | 1472 | 1987 |
| 4 | 54 | 2592 | 3050 | 796 | 1722 | 2287 |
| 4.5 | 46 | 2627 | 3411 | 891 | 1817 | 2595 |
| 5 | 45 | 2602 | 3876 | 979 | 2065 | 2865 |

Example 5

Following the procedures described in example 4 the content of 3-chloro-6-[3,6-dihydro-4-(3-methylphenyl)-1(2H)-pyridinyl]pyridazine was determined in solutions containing various concentrations of γ-CD derivatives. Said pyridazine compound is described in Published Europ. Pat. Appl. No. 0,156,433 as a useful anti-viral agent.

| concentration of γ-CD derivative in % (weight by volume) | content of 3-chloro-6-[3,6-dihydro-4-(3-methylphenyl)-1(2H)-pyridinyl]pryridazine in μg/ml | | |
|---|---|---|---|
| | unsubstituted γ-CD | methyl substituted D.S. = 1.49 | hydroxypropyl substituted M.S. = 0.66 |
| 0 | 0.4 | 0.4 | 0.4 |
| 1 | 2.0 | 2.0 | 1.5 |
| 2.5 | 0.8 | 8.0 | 4.5 |
| 3.5 | — | 12.6 | 7.0 |
| 5 | 0.8 | 20.0 | 10.0 |

C. COMPOSITION EXAMPLES

Example 6

In 100 ml water 7 g hydroxyethyl-γ-CD (M.S.=0.77) and 0.5 g medroxyprogesterone acetate were dissolved. The water was evaporated. 75 mg of the residue was powdered and mixed with 366 mg $CaHPO_4.2H_2O$, 60 mg corn starch, 120 mg cellulose powder (microcrystalline), 4.2 mg highly dispersed silica (Aerosil ® 200) and 4.8 mg magnesium stearate and pressed to a tablet.

Example 7

5 g hydroxyethyl γ-cyclodextrin (M.S.=0.77) and 0.5 g lidocaine were dissolved in 100 ml of a physiological sodium chloride solution at 30° C. and filtered through a membrane filter (0.45 microns). The solution was filled into ampules and sterilized.

What is claimed is:

1. A γ-cyclodextrin ether or mixed ether wherein the ether substituents are $C_1$–$C_6$ alkyl, hydroxy $C_1$–$C_6$ alkyl, carboxy $C_1$–$C_6$-alkyl or ($C_1$–$C_6$ alkyloxycarbonyl) $C_1$–$C_6$ alkyl; provided that hydroxypropyl is not a sole substituent.

2. A γ-cyclodextrin ether or mixed ether according to claim 1 wherein the ether substituents are $C_1$–$C_3$ alkyl, hydroxy $C_2$–$C_4$ alkyl or carboxy $C_1$–$C_2$ alkyl.

3. A γ-cyclodextrin derivative according to claim 1, wherein the ether substituents are methyl, ethyl, isopropyl, hydroxyethyl, hydroxypropyl, hydroxybutyl, carboxymethyl or carboxyethyl.

4. A γ-cyclodextrin ether or mixed ether wherein the ether substituents are $C_1$–$C_3$ alkyl, hydroxy $C_2$–$C_4$ alkyl or carboxy $C_1$–$C_2$ alkyl and wherein the degree of substitution is in the range of 0.125 to 3 and the average molar substitution is in the range of 0.125 to 10.

5. A γ-cyclodextrin derivative according to claim 4, wherein the degree of substitution is in the range of 0.3 to 2 and the average molar substitution is in the range of 0.3 to 3.

6. A γ-cyclodextrin ether or mixed ether wherein the ether substituents are methyl, ethyl, isopropyl, hydroxyethyl, hydroxypropyl, hydroxybutyl, carboxymethyl or carboxyethyl and wherein the degree of substitution is in the range of 0.125 to 3 and the average molar substitution is in the range of 0.125 to 10.

7. A γ-cyclodextrin derivative according to claim 6, wherein the degree of substitution is in the range of 0.3 to 2 and the average molar substitution is in the range of 0.3 to 3.

8. A process for preparing a compound as defined in claim 1, characterized by reacting γ-cyclodextrin with an O-alkylating agent.

9. A process for preparing a compound as defined in claim 2, characterized by reacting γ-cyclodextrin with an O-alkylating agent.

10. A process for preparing a compound as defined in claim 3, characterized by reacting γ-cyclodextrin with an O-alkylating agent.

11. A process according to claim 9, wherein the process is conducted in a reaction-inert solvent in the presence of a base.

12. A process according to claim 9, wherein the process is conducted at a temperature in the range from 30° C. to 200° C.

13. A process according to claim 10, wherein the process is conducted in a reaction-inert solvent in the presence of a base.

14. A process according to claim 10, wherein the process is conducted at a temperature in the range from 30° C. to 200° C.

15. A γ-cyclodextrin ether or mixed ether wherein the ether substituents are $C_1$–$C_6$ alkyl, hydroxy $C_1$–$C_2$ alkyl, hydroxy $C_4$–$C_6$ alkyl, carboxy $C_1$–$C_6$ alkyl or ($C_1$–$C_6$ alkoxy carbonyl) $C_1$–$C_6$ alkyl.

16. A γ-cyclodextrin ether or mixed ether according to claim 15 wherein the ether substituents are $C_1$–$C_3$ alkyl, hydroxy $C_2$ alkyl, hydroxy $C_4$ alkyl, or carboxy $C_1$–$C_2$ alkyl.

17. A γ-cyclodextrin derivative according to claim 15 wherein the either substituents are methyl, ethyl, isopropyl, hydroxyethyl, hydroxybutyl, carboxymethyl, or carboxyethyl.

* * * * *

REEXAMINATION CERTIFICATE (1305th)

United States Patent [19]

Müller

[11] B1 4,764,604

[45] Certificate Issued   Jun. 12, 1990

[54] DERIVATIVES OF GAMMA-CYCLODEXTRIN

[75] Inventor: Bernd W. W. Müller, Flintbek, Fed. Rep. of Germany

[73] Assignee: Janssen Pharmaceutica N.V., Beerse, Belgium

Reexamination Request:
No. 90/001,834, Aug. 31, 1989

Reexamination Certificate for:
Patent No.: 4,764,604
Issued: Aug. 16, 1988
Appl. No.: 833,622
Filed: Feb. 27, 1986

[30] Foreign Application Priority Data

Mar. 15, 1985 [GB] United Kingdom ............... 8506792

[51] Int. Cl.$^5$ .............................................. C08B 37/16
[52] U.S. Cl. .................................... 536/103; 514/58; 514/778; 544/238
[58] Field of Search ................. 536/103; 514/58, 778; 544/238

[56] References Cited

U.S. PATENT DOCUMENTS 4,371,673  2/1983  Pitha ................................ 536/112

OTHER PUBLICATIONS

J. Pitha, "Enhanced Water Solubility of Vitamins A, D, E and K by Substituted Cycloamyloses", Life Science, vol. 29, pp. 307–311, (1981).

Liptak et al, "The Chemistry of Cyclodextrin Derivatives," I. Int. Symp. on Cyclodextrins, (Budapest 1981) pp. 279–287.

J. Pitha et al., "Amorphous Water Soluble Derivatives of Cyclodextrins: Nontoxic Dissolution Enhancing Excipients", J. Pharm. Sci., vol. 74, No. 9 (9/85).

A. P. Croft et al., "Synthesis of Chemically Modified Cyclodextrins", Tetrahedron Report No. 147, vol. 39, No. 9, pp. 1417–1474 (1983).

*Primary Examiner*—Ronald W. Griffin

[57] ABSTRACT

This invention relates to γ-cyclodextrin ethers and mixed ethers wherein the ether substituents are $C_1$–$C_6$ alkyl, hydroxy $C_1$–$C_6$ alkyl, carboxy $C_1$–$C_6$ alkyl or ($C_1$–$C_6$ alkyloxycarbonyl) $C_1$–$C_6$ alkyl; provided that hydroxypropyl is not a sole substituent.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 15, 16 and 17 are cancelled.

Claims 1, 4, 6 and 7 are determined to be patentable as amended.

Claims 2, 3, 5, 8-13 and 14, dependent on an amended claim, are determined to be patentable.

New claims 18 and 19 are added and determined to be patentable.

1. A γ-cyclodextrin ether or mixed ether wherein the ether substituents are $C_1$–$C_6$ alkyl, hydroxy $C_1$–$C_6$ alkyl, carboxy $C_1$–$C_6$-alkyl or ($C_1$–$C_6$ alkyloxycarbonyl) $C_1$–$C_6$ alkyl; provided that *neither methyl nor* hydroxypropyl is [not] a sole substituent.

4. A γ-cyclodextrin [ether or] mixed ether wherein the ether substituents are $C_1$–$C_3$ alkyl, hydroxy $C_2$–$C_4$ alkyl or carboxy $C_1$–$C_2$ alkyl and wherein the degree of substitution is in the range of 0.125 to 3 and the average molar substitution is in the range of 0.125 to 10.

6. A γ-cyclodextrin ether or mixed ether wherein the ether substituents are methyl, ethyl, isopropyl, hydroxyethyl, hydroxypropyl, hydroxybutyl, carboxymethyl or carboxyethyl and wherein the degree of substitution is in the range of 0.125 to [3 and the average molar substitution is in the range of 0.125 to 10] *less than 2*.

7. A γ-cyclodextrin derivative according to claim 6, wherein the [degree of substitution is in the range of 0.3 to 2] *either substituent is hydroxyethyl or hydroxypropyl* and the average molar substitution is in the range of 0.3 to [3] *less than 1*.

*18. A γ-cyclodextrin derivative according to claim 6 wherein the average molar substitution is in the range of 0.125 to 10.*

*19. A γ-cyclodextrin derivative according to claim 18 wherein the average molar substitution is in the range of 0.3 to 3.*

* * * * *